US007227055B2

(12) United States Patent
Spangenberg et al.

(10) Patent No.: US 7,227,055 B2
(45) Date of Patent: Jun. 5, 2007

(54) MANIPULATION OF PLANT SENESCENCE (75) Inventors: German Spangenberg, Bundoora (AU); Yi Han Lin, Singapore (SG); Roger W. Parish, Warrandyte (AU); Song Feng Li, Bulleen (AU); Joshua Heazlewood, East Fremantle (AU); Charles K. Pallaghy, Bundoora (AU)

(73) Assignees: Agriculture Victoria Services Pty, Attwood, Victoria (AU); La Trobe University, Bundoora, Victoria (AU)

( * ) Notice: Subject to any disclaimer, the term of this patent is extended or adjusted under 35 U.S.C. 154(b) by 533 days.

(21) Appl. No.: 10/363,723

(22) PCT Filed: Aug. 30, 2001

(86) PCT No.: PCT/AU01/01092
§ 371 (c)(1),
(2), (4) Date: Jun. 6, 2003

(87) PCT Pub. No.: WO02/20772
PCT Pub. Date: Mar. 14, 2002

(65) Prior Publication Data
US 2004/0025205 A1 Feb. 5, 2004

(30) Foreign Application Priority Data
Sep. 6, 2000 (AU) ................................. PQ9946

(51) Int. Cl.
C12N 15/82 (2006.01)
C12N 5/04 (2006.01)
A01H 5/00 (2006.01)
A01H 5/10 (2006.01)

(52) U.S. Cl. .............. 800/298; 800/278; 800/290; 800/287; 435/320.1; 435/419

(58) Field of Classification Search ............ 800/278, 800/298, 290, 287; 435/320.1, 419, 468; 536/23.1, 23.6, 24.1
See application file for complete search history.

(56) References Cited

U.S. PATENT DOCUMENTS

| 5,512,466 A | 4/1996 | Klee et al. ............ 435/172.3 |
| 5,689,042 A * | 11/1997 | Amasino et al. ............ 800/298 |
| 7,115,798 B1 | 10/2006 | Yadav |
| 7,119,262 B1 | 10/2006 | Smith et al. |

FOREIGN PATENT DOCUMENTS

| CA | 2 263 067 A1 | 8/2000 |
| WO | WO 91/01323 | 2/1991 |
| WO | WO 95/07993 | 3/1995 |
| WO | WO 96/29858 | 3/1996 |
| WO | WO 96/09755 | 4/1996 |
| WO | WO 96/29858 | 10/1996 |
| WO | WO 97/47756 | 12/1997 |
| WO | WO 98/44781 | 10/1998 |
| WO | WO 99/06571 | 2/1999 |
| WO | WO 99/06580 | 2/1999 |
| WO | WO 00/00598 | 1/2000 |
| WO | WO 00/42171 | 7/2000 |
| WO | WO 00/49164 | 8/2000 |
| WO | WO 00/70061 | 11/2000 |
| WO | WO 01/02592 | 1/2001 |
| WO | WO 01/16332 A1 | 3/2001 |
| WO | WO 01/30143 A2 | 5/2001 |
| WO | WO 01/96580 A2 | 12/2001 |
| WO | WO 01/98510 | 12/2001 |
| WO | WO 02/42440 A2 | 5/2002 |
| WO | WO 02/44392 A2 | 6/2002 |
| WO | WO 02/45486 A1 | 6/2002 |
| WO | WO 02/099079 A2 | 12/2002 |

OTHER PUBLICATIONS

Kranz, et al., "Towards Functional Characterisation of the Members of the R2R3-MYB Gene . . . ," Plant Journal, Blackwell Sci. Pub., Oxford, GB, vol. 16, No. 2., 98, pp. 263-276.
Lanahan et al., "A Gibberellin Response Complex in Cereal Alpha-Amylase . . . ," Plant Cell, American. Soc. of Plant Phys., Rockville, MD, US, vol. 4, 1992, pp. 203-211.
Li, Song Feng, et al., "A Novel MYB-Related Gene from *Arabidopsis thaliana*," Febs Letters, Elsevier Science Publishers, Amsterdam, NL, vol. 373, 1996, pp. 117-121.
Woodger, M.B., et al., "The role of GAMYB transcription factors in GB-regulated gene expression," Journal of Plant Growth Regulation, vol. 22, No. 2, 2003, pp. 176-184.
Gan and Amasino (1995), Inhibition of leaf senescence by autoregulated production of cytokinin. Science 270:1986.
Gan and Amasino (1999), Developmental targeting of gene expression by the use of a senescence specific promoter, In. Inducible gene expression in plants, Reynolds, PHS (ed) CABI Publishing. Wallingford, UK.
Li et al., (1999) Cloning of three MYB-like genes from *Arabidopsis thaliana* (PGR 99-138) Plant Physiol. 121:313.
Smart, Catherine M. et al., Delayed Leaf Senescence in Tobacco Plants Transformed with *tmr*, a Gene for Cytokinin Production in *Agrobacterium*. The Plant Cell, vol. 3, 647-656, Jul. 1991.
Zbang et al., (2000) Development of flooding-tolerant *Arabidopsis thaliana* by autoregulated cytokinin production. Mol. Breeding 6:135-144.

* cited by examiner

*Primary Examiner*—Stuart F. Baum
(74) *Attorney, Agent, or Firm*—David A. Farah; Sheldon Mak Rose & Anderson PC (57) ABSTRACT

The present invention relates to methods of manipulating senescence in plants. The invention also relates to vectors useful in such methods, transformed plants with modified senescence characteristics and plant cells, seeds and other parts of such plants.

6 Claims, 6 Drawing Sheets

```
  1 gtttgtgtct tctagattaa tcctccaaac ttttgattaa ccaaaaaaat tatcaaacta
 61 acatgttctc cttttttctt tagaaattct aacgaattta tctttatact gatttgaata
121 tacttaattt ggtcatttgg atgcccttta caacctcctt accaaactca ctatggcaaa
181 tatatactat tttccattgt aacataaatg tccataattt gaattaaatt cgttgcagta
241 cgaaaccatc caactttgtc caaaaacaaa atccttataa ctatttactt taatgtaaat
301 atatcctcta cttttgtttt tacaaccctg gctcaaacaa atttattatt tgcgataaaa
361 aatcatatcg aacaaactcg atgatttttt ttttcttacg ttattaatga aactaaaata
421 tagaaaaaaa caagatgaac caaattttca cctatctaac tacttaaata taatatgatt
481 aaatttggta aagtttgaaa agtttcttta gaaatgtgaa atattgatca cagtttctat
541 tgctaaaatc accaacaaaa cgcatgtcgc cattcataat tatggtttca cacctacaac
601 taggctaata agtaaataag tagacaacta gactcaggtt tgaaaaaacc ataaaagcca
661 tatagcgttt tctcattgaa actgcgaaca cgatcgtgtg aatgttgcag tttctagttt
721 tgatacaaac aaacaaaaac acaatttaat cttagattaa aaagaaaaaa gagaacggag
781 cccactagcc actccttcaa acgtgtctta ccaactctct tctagaaaca aattaggctt
841 caccttcctc ttccaacctc tctctctctc tctctctctt tttctcaaac catctctcca
901 taaagcccta atttcttcat cacaagaatc agaagaagaa a
```

FIGURE 1

```
   1 ggatcctgtt acaagtattg caagtcttat aaattgcata ttaatgcaat cttgattttt
  61 aacaacgaac gtaatgggqt aaaaaatgta tgttatatta tttatattta attatattgg
 121 agtgcgccat aatatgatga tttataatta aaaaatattt actgtcacat tgactgagat
 181 ggcactgtta tttcaaccat gaaattttgt tgattttttt acaataacaa taattgcagg
 241 aagtaaataa tagacgccgt tgttaaaaaa ttgcaatcat atgtgcctaa ctatagggac
 301 aattaagtca attgtaatag tctcccttat tttaacgact cacctaatca agtattacaa
 361 aatatctcac ttttcgtcag taatgatgta atcagaactg aatagtacaa gtaaaacgtg
 421 gaaaaacgtc atagagtggc atgattatat tcctctgcat tgccaattta ttcagcttta
 481 tttgacttag gtgtgccttc gttagcgaca aattgctttc aaggagacag ccatgcccca
 541 cactttgttg aaaaacaagt tgcctttcgg gatacggtaa agccagttgc acttcaataa
 601 tgaatttcaa ggagacaata taaccgcctc tgataacaca attctctaat ataaaaatca
 661 gtttgtattc aatatactgc aaaaaactta tggacctgca tctaattttc ggtccaactt
 721 gcacaggaaa gacgacgacc gcgatagctc ttgcccagca gacagggctt ccagtccttt
 781 cgcttgatcg ggtccaatgc tgtcctcaac tatcaaccgg aagcggacga ccaacagtgg
 841 aagaactgaa aggaacgacg cgtctctacc ttgatgatcg gcctctggtg gagggtatca
 901 tcgcagccaa gcaagctcat cataggctga tcgaggaggt gtataatcat gaggccaacg
 961 gcgggcttat tcttgaggga ggatccacct cgttgctcaa ctgcatggcg cgaaacagct
1021 attggagtgc agattttcgt tggcatatta ttcgccacaa gttacccgac caagagacct
1081 tcatgaaagc ggccaaggcc agagttaagc agatgttgca cccgctgca ggccattcta
1141 ttattcaaga gttggtttat ctttggaatg aacctcggct gaggcccatt ctgaaagaga
1201 tcgatggata tcgatatgcc atgttgtttg ctagccagaa ccagatcacg gcagatatgc
1261 tattgcagct tgacgcaaat atggaaggta agttgattaa tgggatcgct caggagtatt
1321 tcatccatgc gcgccaacag gaacagaaat tcccccaagt taacgcagcc gctttcgacg
1381 gattcgaagg tcatccgttc ggaatgtatt aggttacgcc agccctgcgt cgcacctgtc
1441 ttcatctgga taagatgttc gtaattgttt ttggctttgt cctgttgtgg cagggcggca
1501 aatacttccg acaatccatc gtgtcttcaa actttatgct ggtgaacaag tcttagtttc
1561 cacgaaagta ttatgttaaa ttttaaaatt tcgatgtata atgtggctat aattgtaaaa
1621 ataaactatc gtaagtgtgc gtgttatgta taatttgtct aaatgtttaa tatatatcat
1681 agaacgcaat aaatattaaa tatagcgctt ttatgaaata taaatacatc attacaagtt
1741 gtttatattt cgggtacctt ttccattatt ttgcgcaaca agtcacggat attcgtgaaa
1801 acgacaaaaa ctgcgaaatt tgcgggcagt gccttcagtt ttcctattaa tatttagttt
1861 gacaccagtt gctatcattg cggccaagct cagctgtttc ttttcttgaa acgatggatc
1921 gaatgagcat ggctcggcaa ggttggcttg taccatgtct ttctcatggc aaagatgatc
1981 aactgcag
```

| Genotype | HC | Hmq | 01 | 08 |
|---|---|---|---|---|
| Week1 | 8/30 | 9/31 | 3/30 | 0/29 |
| Week2 | 21/30 | 19/31 | 9/30 | 4/29 |

| Genotype | HC | Hmq | 11 | 12 | 16 | 18 |
|---|---|---|---|---|---|---|
| Week1 | 9/30 | 5/36 | 0/39 | 0/36 | 4/39 | 1/36 |
| Week2 | 19/30 | 15/36 | 1/39 | 1/36 | 17/39 | 5/36 |

SEQUENCE LISTING

<160> NUMBER OF SEQ ID NOS: 2

<210> SEQ ID NO 1
<211> LENGTH: 941
<212> TYPE: DNA
<213> ORGANISM: Arabidopsis thaliana

<400> SEQUENCE: 1

```
gtttgtgtct tctagattaa tcctccaaac ttttgattaa ccaaaaaaat tatcaaacta      60
acatgttctc cttttttctt tagaaattct aacgaattta tctttatact gatttgaata     120
tacttaattt ggtcatttgg atgccttta caacctcctt accaaactca ctatggcaaa     180
tatatactat tttccattgt aacataaatg tccataattt gaattaaatt cgttgcagta     240
cgaaaccatc caactttgtc caaaaacaaa atccttataa ctatttactt taatgtaaat     300
atatcctcta cttttgtttt tacaacccta gctcaaacaa atttattatt tgcgataaaa     360
aatcatatcg aacaaactcg atgatttttt ttttcttacg ttattaatga aactaaaata     420
tagaaaaaaa caagatgaac caaattttca cctatctaac tacttaaata taatatgatt     480
aaatttggta agtttgaaa agtttcttta gaaatgtgaa atattgatca cagtttctat     540
tgctaaaatc accaacaaaa cgcatgtcgc cattcataat tatggtttca cacctacaac     600
taggctaata agtaaataag tagacaacta gactcaggtt tgaaaaaacc ataaaagcca     660
tatagcgttt tctcattgaa actgcgaaca cgatcgtgtg aatgttgcag tttctagttt     720
tgatacaaac aaacaaaaac acaatttaat cttagattaa aaagaaaaaa gagaacggag     780
cccactagcc actccttcaa acgtgtctta ccaactctct tctagaaaca aattaggctt     840
caccttcctc ttccaacctc tctctctctc tctctctctt tttctcaaac catctctcca     900
taaagcccta atttcttcat cacaagaatc agaagaagaa a                        941
```

<210> SEQ ID NO 2
<211> LENGTH: 1988
<212> TYPE: DNA
<213> ORGANISM: Agrobacterium tumefaciens

<400> SEQUENCE: 2

```
ggatcctgtt acaagtattg caagttttat aaattgcata ttaatgcaat cttgattttt      60
aacaacgaac gtaatggcgt aaaaaatgta tgttatatta tttatattta attatattgg     120
agtgcgccat aatatgatga tttataatta aaaaatattt actgtcacat tgactgagat     180
ggcactgtta tttcaaccat gaaattttgt tgatttttt acaataacaa taattgcagg     240
aagtaaataa tagacgccgt tgttaaaaaa ttgcaatcat atgtgcctaa ctataggac      300
aattaagtca attgtaatag tctcccttat tttaacgact cacctaatca agtattacaa     360
aatatctcac ttttcgtcag taatgatgta atcagaactg aatagtacaa gtaaaacgtg     420
gaaaaacgtc atagagtggc atgattatat tcctctgcat tgccaattta ttcagcttta     480
tttgacttag gtgtgccttc gttagcgaca aattgctttc aaggagacag ccatgcccca     540
cactttgttg aaaaacaagt tgccttttgg gatacggtaa agccagttgc acttcaataa     600
tgaatttcaa ggagacaata taaccgcctc tgataacaca attctctaat ataaaaatca     660
```

-continued

```
gtttgtattc aatatactgc aaaaaactta tggacctgca tctaattttc ggtccaactt      720
gcacaggaaa gacgacgacc gcgatagctc ttgcccagca gacagggctt ccagtccttt      780
cgcttgatcg ggtccaatgc tgtcctcaac tatcaaccgg aagcggacga ccaacagtgg      840
aagaactgaa aggaacgacg cgtctctacc ttgatgatcg gcctctggtg gagggtatca      900
tcgcagccaa gcaagctcat cataggctga tcgaggaggt gtataatcat gaggccaacg      960
gcgggcttat tcttgaggga ggatccacct cgttgctcaa ctgcatggcg cgaaacagct     1020
attggagtgc agattttcgt tggcatatta ttcgccacaa gttacccgac caagagacct     1080
tcatgaaagc ggccaaggcc agagttaagc agatgttgca ccccgctgca ggccattcta     1140
ttattcaaga gttggtttat ctttggaatg aacctcggct gaggcccatt ctgaaagaga     1200
tcgatggata tcgatatgcc atgttgtttg ctagccagaa ccagatcacg gcagatatgc     1260
tattgcagct tgacgcaaat atggaaggta agttgattaa tgggatcgct caggagtatt     1320
tcatccatgc gcgccaacag gaacagaaat tcccccaagt taacgcagcc gctttcgacg     1380
gattcgaagg tcatccgttc ggaatgtatt aggttacgcc agccctgcgt cgcacctgtc     1440
ttcatctgga taagatgttc gtaattgttt ttggctttgt cctgttgtgg cagggcggca     1500
aatacttccg acaatccatc gtgtcttcaa actttatgct ggtgaacaag tcttagtttc     1560
cacgaaagta ttatgttaaa ttttaaaatt tcgatgtata atgtggctat aattgtaaaa     1620
ataaactatc gtaagtgtgc gtgttatgta taatttgtct aaatgtttaa tatatatcat     1680
agaacgcaat aaatattaaa tatagcgctt ttatgaaata taaatacatc attacaagtt     1740
gtttatattt cgggtacctt ttccattatt ttgcgcaaca agtcacggat attcgtgaaa     1800
acgacaaaaa ctgcgaaatt tgcgggcagt gccttcagtt ttcctattaa tatttagttt     1860
gacaccagtt gctatcattg cggccaagct cagctgtttc ttttcttgaa acgatggatc     1920
gaatgagcat ggctcggcaa ggttggcttg taccatgtct ttctcatggc aaagatgatc     1980
aactgcag                                                             1988
```

MANIPULATION OF PLANT SENESCENCE

CROSS-REFERENCE TO RELATED APPLICATION

This application claims priority from International Patent Application PCT/AU 01/01092, entitled "Manipulation of Plant Senescence Using An MYB Gene Promoter and Cytokinin Biosynthesis Genes," filed Aug. 30, 2001, which claims priority from Australian Patent Application PQ 9946, entitled "Manipulation of Plant Senescence Using An MYB Gene Promoter and Cytokinin Biosynthesis Genes," filed Sep. 6, 2000; the contents of which are incorporated by reference herein in its entirety.

The present invention relates to methods of manipulating senescence in plants. The invention also relates to vectors useful in such methods, transformed plants with modified senescence characteristics and plant cells, seeds and other parts of such plants.

Leaf senescence involves metabolic and structural changes in cells prior to cell death. It also involves the recycling of nutrients to actively growing regions.

The regulation of plant and plant organ senescence by cytokinins has important agricultural consequences. Elevated cytokinin levels in leaves tend to retard senescence. A number of promoters have been used to regulate the expression of the ipt gene, whose product (isopentenyltransferase) catalyses a key step in cytokinin synthesis. However, in general, transgenic plants over-expressing the ipt gene have been reported to have retarded root and shoot growth, no root formation, reduced apical dominance, and reduced leaf area.

It is an object of the present invention to overcome, or at least alleviate, one or more of the difficulties or deficiencies associated with the prior art.

In one aspect, the present invention provides a method of manipulating senescence in a plant, said method including introducing into said plant a genetic construct including a myb gene promoter, or a functionally active fragment or variant thereof, operatively linked to a gene encoding an enzyme involved in biosynthesis of a cytokinin, or a functionally active fragment or variant thereof.

The manipulation of senescence relates to the plant and/or specific plant organs. Senescence of different plant organs, such as leaves, roots, shoots, stems, tubers, flowers, stolons, and fruits may be manipulated. The manipulation of plant and plant organ senescence may have important agricultural consequences, such as increased shelf life of e.g. fruits, flowers, leaves and tubers in horticultural produce and cut flowers, reduced perishability of horticultural crops, increased carbon fixation in senescence-retarded leaves leading to enhanced yields, enhanced biomass production in forage plants, enhanced seed production, etc.

"Manipulating senescence" generally relates to delaying senescence in the transformed plant relative to an untransformed control plant. However, for some applications it may be desirable to promote or otherwise modify senescence in the plant. Senescence may be promoted or otherwise modified for example, by utilizing an antisense gene.

An effective amount of said genetic construct may be introduced into said plant, by any suitable technique, for example by transduction, transfection or transformation. By "an effective amount" is meant an amount sufficient to result in an identifiable phenotypic trait in said plant, or a plant, plant seed or other plant part derived therefrom. Such amounts can be readily determined by an appropriately skilled person, taking into account the type of plant, the route of administration and other relevant factors. Such a person will readily be able to determine a suitable amount and method of administration. See, for example, Maniatis et al, Molecular Cloning: A Laboratory Manual, Cold Spring Harbor Laboratory, Cold Spring Harbor, the entire disclosure of which is incorporated herein by reference.

Figure 1:
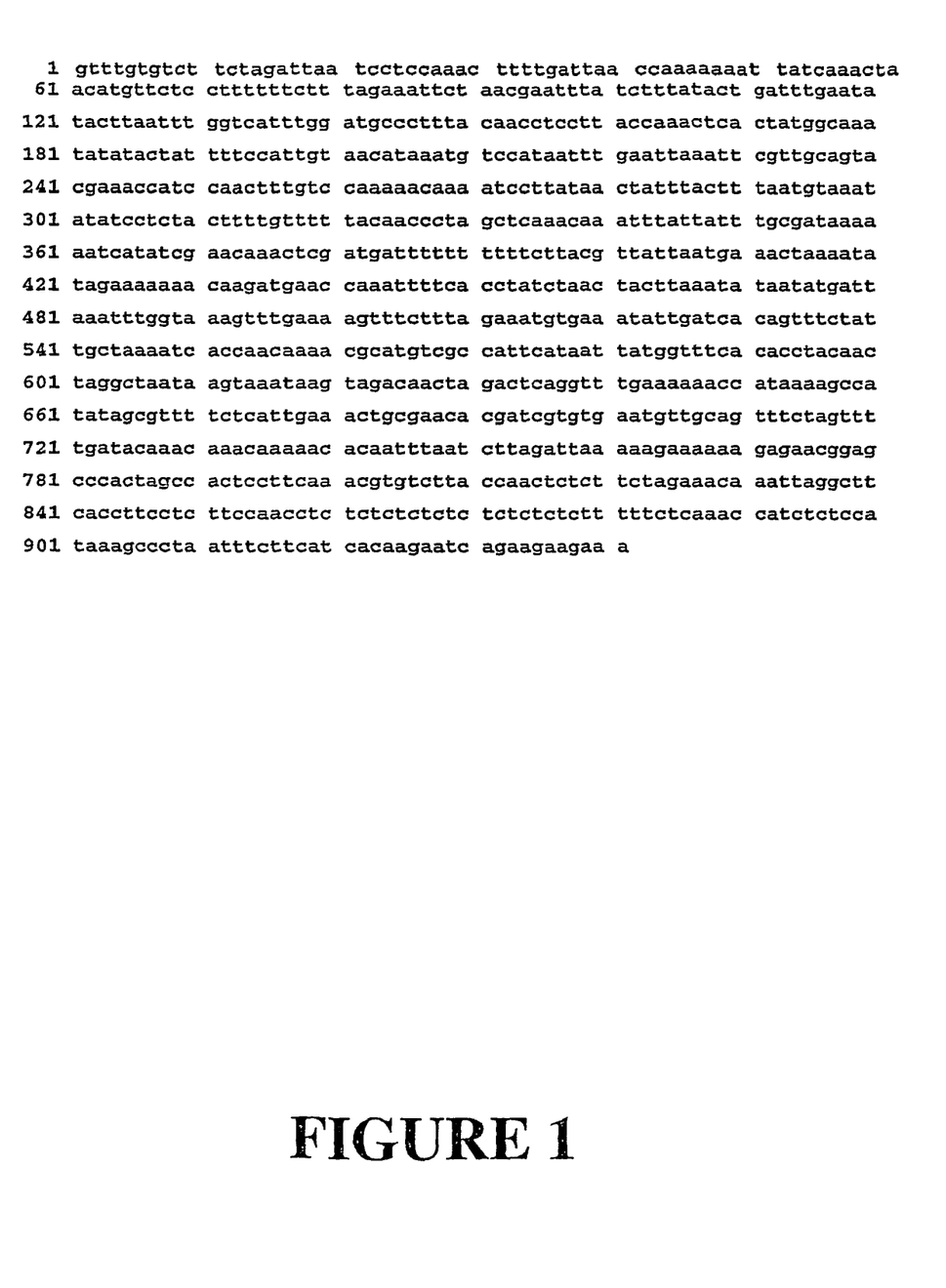
FIG. 1 shows the nucleotide sequence of the promoter from myb32 gene (atmyb32) from *Arabidopsis thaliana* (Sequence ID No: 1).

Preferably the myb gene promoter is a myb32 promoter. Preferably the myb gene promoter is from *Arabidopsis*, more preferably *Arabidopsis thaliana*. Most preferably the myb gene promoter includes a nucleotide sequence selected from the group consisting of the sequence shown in FIG. 1 hereto (Sequence ID No: 1) and functionally active fragments and variants thereof.

A suitable promoter is described in Li et al., Cloning of three MYB-like genes from *Arabidopsis* (PGR 99–138) Plant Physiology 121:313 (1999), the entire disclosure of which is incorporated herein by reference.

By "functionally active" is meant that the fragment or variant (such as an analogue, derivative or mutant) is capable of manipulating senescence in a plant by the method of the present invention. Such variants include naturally occurring allelic variants and non-naturally occurring variants. Additions, deletions, substitutions and derivatizations of one or more of the nucleotides are contemplated so long as the modifications do not result in loss of functional activity of the fragment or variant. Preferably the functionally active fragment or variant has at least approximately 80% identity to the relevant part of the above mentioned sequence, more preferably at least approximately 90% identity, most preferably at least approximately 95% identity. Preferably the fragment has a size of at least 10 nucleotides, more preferably at least 15 nucleotides, most preferably at least 20 nucleotides.

The gene encoding an enzyme involved in biosynthesis of a cytokinin may be of any suitable type. Preferably the gene is an isopentenyl transferase (ipt) gene. Preferably the gene is from *Agrobacterium*, more preferably *Agrobacterium tumefaciens*. Most preferably the gene includes a nucleotide sequence selected from the group consisting of the sequence shown in FIG. 2 hereto (Sequence ID No: 2) and functionally active fragments and variants thereof.

By "functionally active" is meant that the fragment or variant (such as an analogue, derivative or mutant) is capable of manipulating senescence in a plant by the method of the present invention. Such variants include naturally occurring allelic variants and non-naturally occurring variants. Additions, deletions, substitutions and derivatizations of one or more of the nucleotides are contemplated so long as the modifications do not result in loss of functional activity of the fragment or variant. Preferably the functionally active fragment or variant has at least approximately 80% identity to the relevant part of the above mentioned sequence, more preferably at least approximately 90% identity, most preferably at least approximately 95% identity. Such functionally active variants and fragments include, for example, those having nucleic acid changes which result in conservative amino acid substitutions of one or more residues in the corresponding amino acid sequence. Preferably the fragment has a size of at least 10 nucleotides, more preferably at least 15 nucleotides, most preferably at least 20 nucleotides.

The genetic construct may be introduced into the plant by any suitable technique. Techniques for incorporating the genetic constructs of the present invention into plant cells (for example by transduction, transfection or transformation) are well known to those skilled in the art. Such techniques include *Agrobacterium* mediated introduction, electroporation to tissues, cells and protoplasts, protoplast fusion, injection into reproductive organs, injection into immature embryos and high velocity projectile introduction to cells, tissues, calli, immature and mature embryos, and combinations thereof. The choice of technique will depend largely on the type of plant to be transformed, and may be readily determined by an appropriately skilled person.

Cells incorporating the genetic construct of the present invention may be selected, as described below, and then cultured in an appropriate medium to regenerate transformed plants, using techniques well known in the art. The culture conditions, such as temperature, pH and the like, will be apparent to the person skilled in the art. The resulting plants may be reproduced, either sexually or asexually, using methods well known in the art, to produce successive generations of transformed plants.

The method of the present invention may be applied to a variety of plants, including monocotyledons [such as grasses (forage and turfgrasses), corn, oat, wheat and barley)], dicotyledons [such as *Arabidopsis*, tobacco, clovers (e.g. white clover, red clover, subterranean clover), alfalfa, canola, vegetable brassicas, lettuce, spinach] and gymnosperms.

In a second aspect of the present invention there is provided a vector capable of manipulating senescence in a plant, said vector including a myb gene promoter, or a functionally active fragment or variant thereof, operatively linked to a gene encoding an enzyme involved in the biosynthesis of a cytokinin, or a functionally active fragment or variant thereof.

In a preferred embodiment of this aspect of the invention, the vector may further include a terminator; said promoter, gene and terminator being operatively linked.

By "operatively linked" is meant that said promoter is capable of causing expression of said gene in a plant cell and said terminator is capable of terminating expression of said gene in a plant cell. Preferably, said promoter is upstream of said gene and said terminator is downstream of said gene.

The vector may be of any suitable type and may be viral or non-viral. The vector may be an expression vector. Such vectors include chromosomal, non-chromosomal and synthetic nucleic acid sequences, eg. derivatives of plant viruses; bacterial plasmids; derivatives of the Ti plasmid from *Agrobacterium tumefaciens*; derivatives of the Ri plasmid from *Agrobacterium rhizogenes*; phage DNA; yeast artificial chromosomes; bacterial artificial chromosomes; binary bacterial artificial chromosomes; vectors derived from combinations of plasmids and phage DNA. However, any other vector may be used as long as it is replicable or integrative or viable in the plant cell.

The promoter, gene and terminator may be of any suitable type and may be endogenous to the target plant cell or may be exogenous, provided that they are functional in the target plant cell.

A variety of terminators which may be employed in the vectors of the present invention are also well known to those skilled in the art. The terminator may be from the same gene as the promoter sequence or a different gene. Particularly suitable terminators are polyadenylation signals, such as the CaMV 35S polyA and other terminators from the nopaline synthase (nos) and the octopine synthase (ocs) genes.

The vector, in addition to the promoter, the gene and the terminator, may include further elements necessary for expression of the gene, in different combinations, for example vector backbone, origin of replication (ori), multiple cloning sites, spacer sequences, enhancers, introns (such as the maize Ubiquitin Ubi intron), antibiotic resistance genes and other selectable marker genes [such as the neomycin phosphotransferase (nptll) gene, the hygromycin phosphotransferase (hph) gene, the phosphinothricin acetyltransferase (bar or pat) gene], and reporter genes (such as beta-glucuronidase (GUS) gene (gusA)]. The vector may also contain a ribosome binding site for translation initiation. The vector may also include appropriate sequences for amplifying expression.

As an alternative to use of a selectable marker gene to provide a phenotypic trait for selection of transformed host cells, the presence of the vector in transformed cells may be determined by other techniques well known in the art, such as PCR (polymerase chain reaction), Southern blot hybridisation analysis, histochemical assays (e.g. GUS assays), thin layer chromatography (TLC), northern and western blot hybridisation analyses.

Those skilled in the art will appreciate that the various components of the vector are operatively linked, so as to result in expression of said gene. Techniques for operatively linking the components of the vector of the present invention are well known to those skilled in the art. Such techniques include the use of linkers, such as synthetic linkers, for example including one or more restriction enzyme sites.

In a further aspect of the present invention there is provided a transgenic plant cell, plant, plant seed or other plant part, with modified senescence characteristics. Preferably the transgenic plant cell, plant, plant seed or other plant part is produced by a method according to the present invention.

The present invention also provides a plant, plant seed or other plant part derived from a plant cell of the present invention.

The present invention also provides a plant, plant seed or other plant part derived from a plant of the present invention.

The present invention will now be more fully described with reference to the accompanying examples and drawings. It should be understood, however, that the description following is illustrative only and should not be taken in any way as a restriction on the generality of the invention described above.

In the figures:

The patent or application file contains at least one drawing executed in color. Copies of this patent or patent application publication with color drawings will be provided by the Office upon request and payment of the necessary fee.

FIG. 2 shows the nucleotide sequence of the isopentenyl transferase (ipt) gene from *Agrobacterium tumefaciens* (Sequence ID No: 2).

FIG. 3 shows PCR and Southern DNA analysis of atmyb32::ipt transgenic white clover (*Trifolium repens*) plants. a) The T-DNA region of patmyb32:ipt showing restriction enzyme sites and location of the probes used for Southern hybridization analysis. b) Ethidium bromide stained 1% agarose gel of the PCR amplified 599 bp nptll and 583 bp ipt products. c) Southern blot hybridization with HindIII digested total genomic DNA isolated from PCR positive white clover plants hybridized with the ipt probe. d) Southern blot hybridization with HindIII digested total genomic DNA isolated from PCR positive white clover plants hybridized with the nptll probe. Lanes 1–2: two independent kanamycin resistant cv. Haifa regenerants, code: Hmi01, Hmi08 respectively; Lanes 3–12: twelve independent kanamycin resistant cv. Irrigation regenerants, codes: Imi06, Imi07, Imi08, Imi09, Imi10, Imi11, Imi12, Imi14, Imi16, Imi18 respectively; Lane C: non-transformed white clover; Lane P: positive control plasmid patmyb32ipt.

EXAMPLES

Example 1

Production of atmyb32::ipt Transgenic Plants

Figure 3:
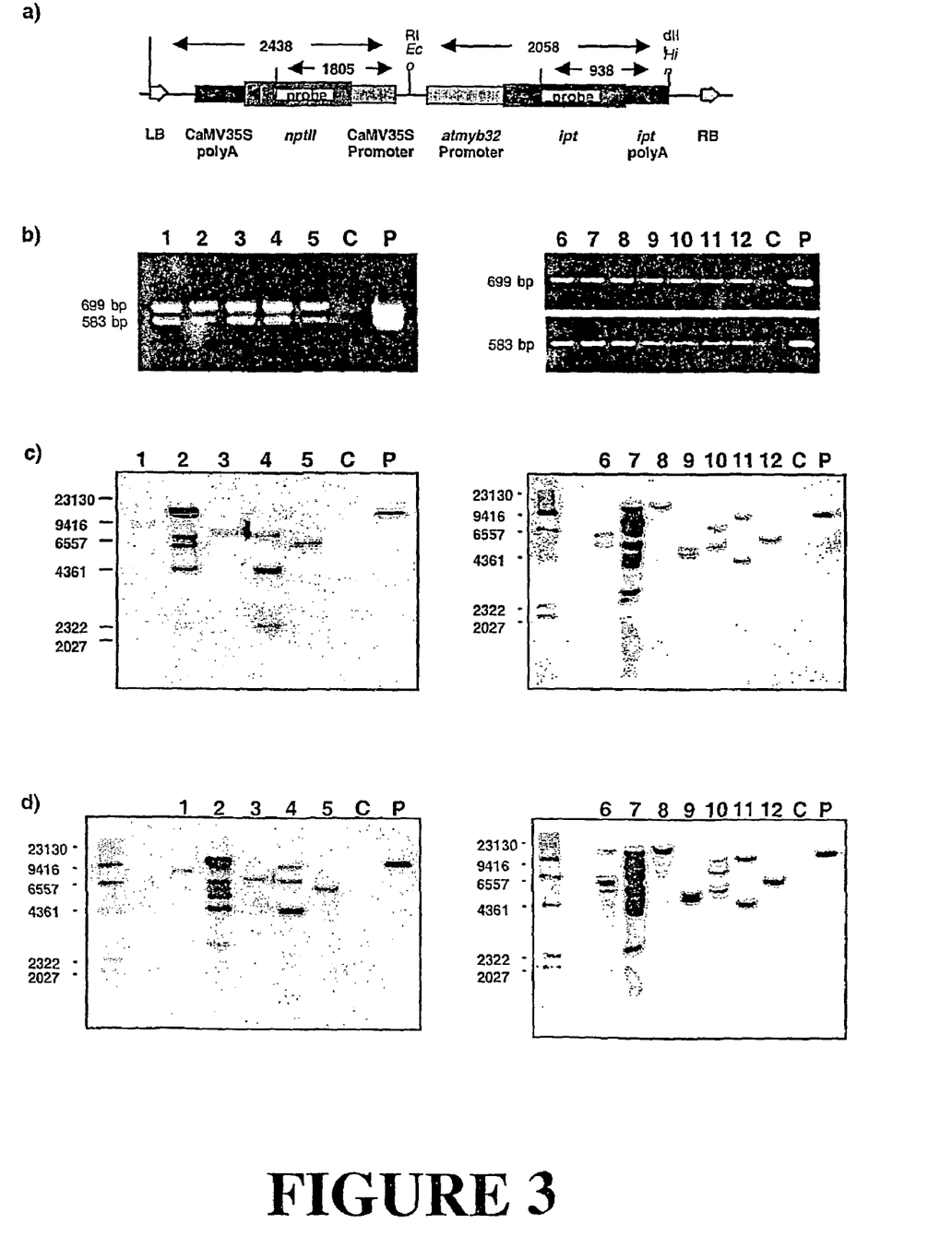

Transgenic white clover plants (*Trofolium repens* cv. Haifa and Irrigation) were produced by *Agrobacterium*-mediated transformation using a binary vector carrying the chimeric atmyb32::ipt gene (FIG. 3a). The transgenic plants were screened by PCR using ipt and nptll primers (FIG. 3b). HindIII digested genomic DNA samples subjected to Southern DNA hybridization analysis showed that the DNA fragments greater than 4.4 kb were detected in all lanes by both ipt and nptll probes, demonstrating the presence and integration of full-length T-DNA into the white clover genome (FIG. 3). Transgenic lines Hmi01, Imi06, Imi11, and Imi18 (Lane 1, 3, 5, 8 and 12 respectively) appeared to have a single copy of full-length T-DNA integrated in the genome. Other transgenic lines had multiple copies of the atmyb32::ipt transgene.

Example 2

Expression of atmyb32::ipt Gene in Transgenic Plants

Figure 4:
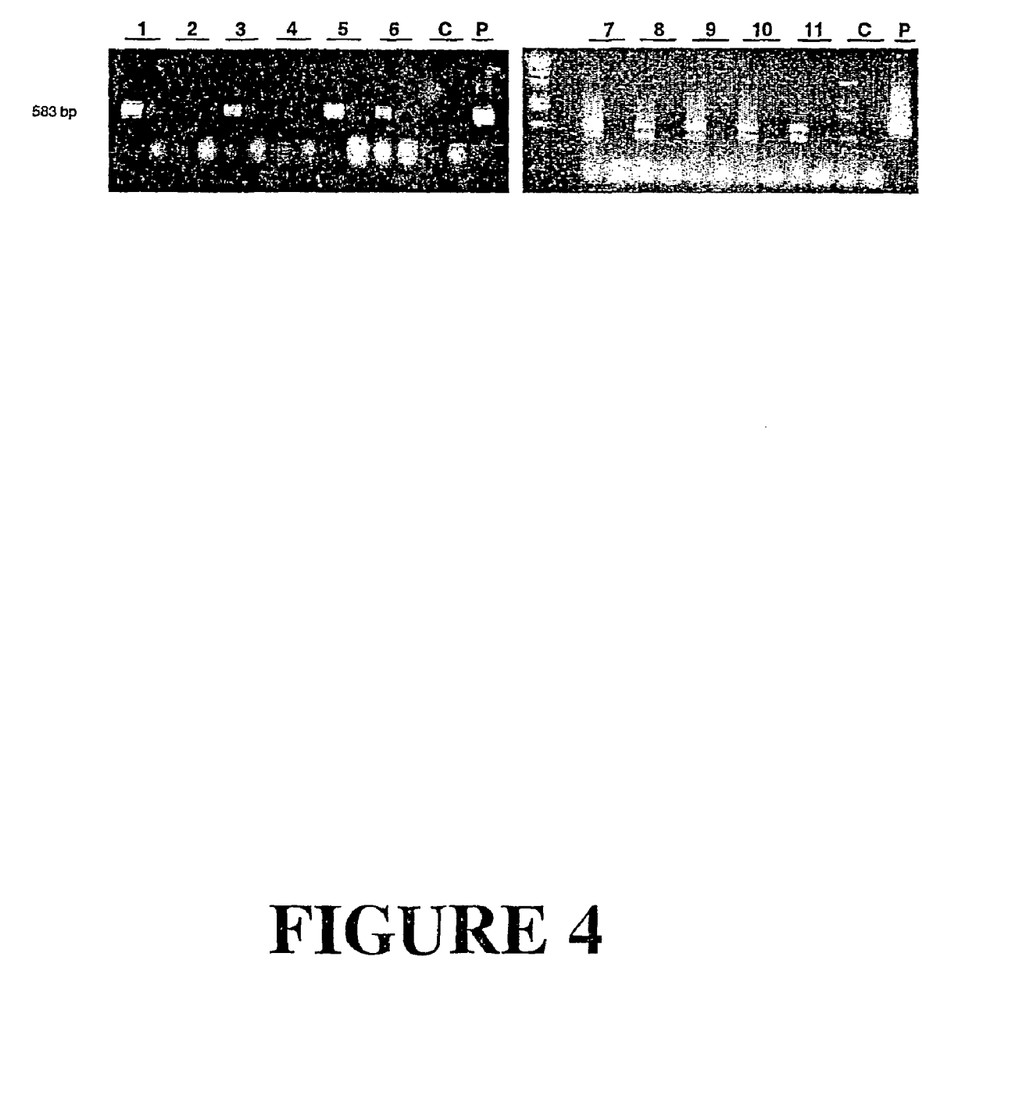
FIG. 4 shows RT-PCR analysis of ipt mRNA expression in atmyb32::ipt transgenic white clover (*T. repens*) plants. Lane 1–11 are samples from 11 independent transgenic lines with corresponding plant codes as in FIG. 4.8; Lane C, Control non-transformed plant; Lane P, plasmid as positive control. Total RNA was isolated from leaf tissues. Total RNA (13 μg) was used for each reverse transcription reaction and ⅕ of RT product was amplified by PCR. DNA products on the gel on the right were amplified by 2×30 cycles intensive PCR. No reverse transcriptase was added to the corresponding RT-PCR reaction loaded into alternate lanes.

The expression of the atmyb32::ipt transgene in transgenic white clover (*T. repens*) plants was assessed by RT-PCR. The ipt mRNA was detected in leaf tissues of all atmyb32::ipt transgenic white clover plants examined, with varying levels of PCR products detected (FIG. 4).

Example 3

Delayed Detached Leaf Senescence in atmyb32::ipt Transgenic Plants

Figure 5:
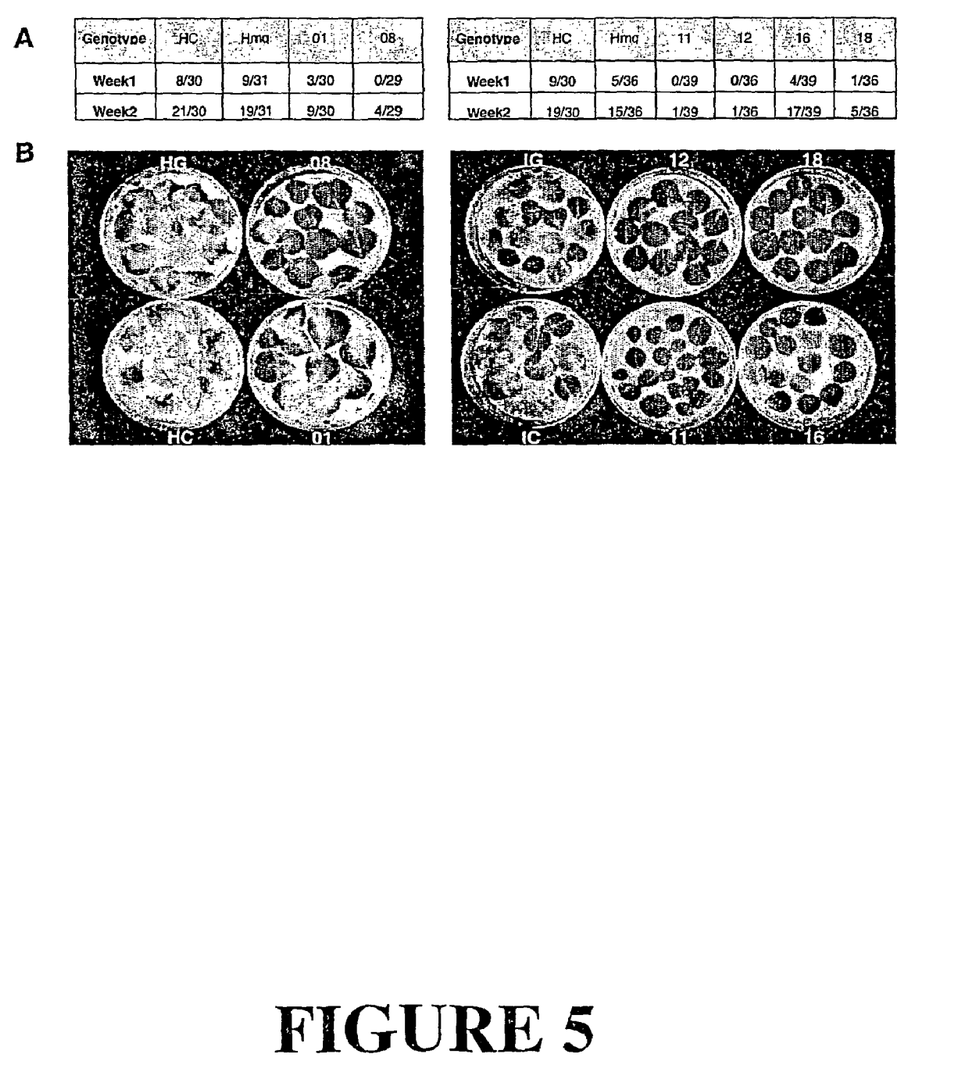
FIG. 5 shows a senescence bioassay of excised leaves from atmyb32::ipt transgenic white clover (*T. repens*) plants. At least 30 leaves were collected from each line from similar positions on stolons of plant lines. A. The number of yellowing leaves as a fraction of the total number of excised leaves. B. Typical appearance of leaves kept on water under light for two weeks. Key to plant lines: HC, IC and Hmg, Img, non-transformed and atmyb32::gusA transgenic plants (cv. Haifa and Irrigation) respectively; 01 and 08, atmyb32::ipt transgenic Haifa lines Hmi01 and Hmi08 respectively; 11, 12, 16 and 18 atmyb32::ipt transgenic Irrigation lines Imi11, Imi12, Imi16 and Imi18 respectively.

Experiments were performed to assess detached leaf senescence of atmyb32::ipt transgenic plants. Rapid yellowing was observed in detached leaves from non-transformed and atmyb32::gusA transgenic white clover plants of both cultivars within one week. Transgenic lines Hmi01, Hmi08, Imi16 and Imi18 showed delayed senescence while Imi11 and Imi12 showed no sign of yellowing by the end of 7 days. After two weeks, the leaves of all atmyb32::ipt transgenic plants were much greener than those of non-transformed and atmyb32::gusA control transgenic plants (FIG. 5). The degree of senescence in excised leaves was in the order HC, Hmg>Hmi01>Hmi08 for cv. Haifa, and IC and Img>Imi16>Imi18>Imi11 and Imi12 for cv. Irrigation. HC is Haifa untransformed control, Hmg is Haifa atmyb32::gusA control, IC is Irrigation untransformed control, Img is Irrigation atmyb32::gusA control. Hmi01, Hmi08, Imi16, Imi18, Imi11 and Imi12 are independent atmyb32::ipt transgenic white clover plants from the cultivar Haifa (H) and Irrigation (I), respectively.

Example 4

Normal Plant Morphology and Root Development in atmyb32::ipt Transgenic Plants

Figure 6:
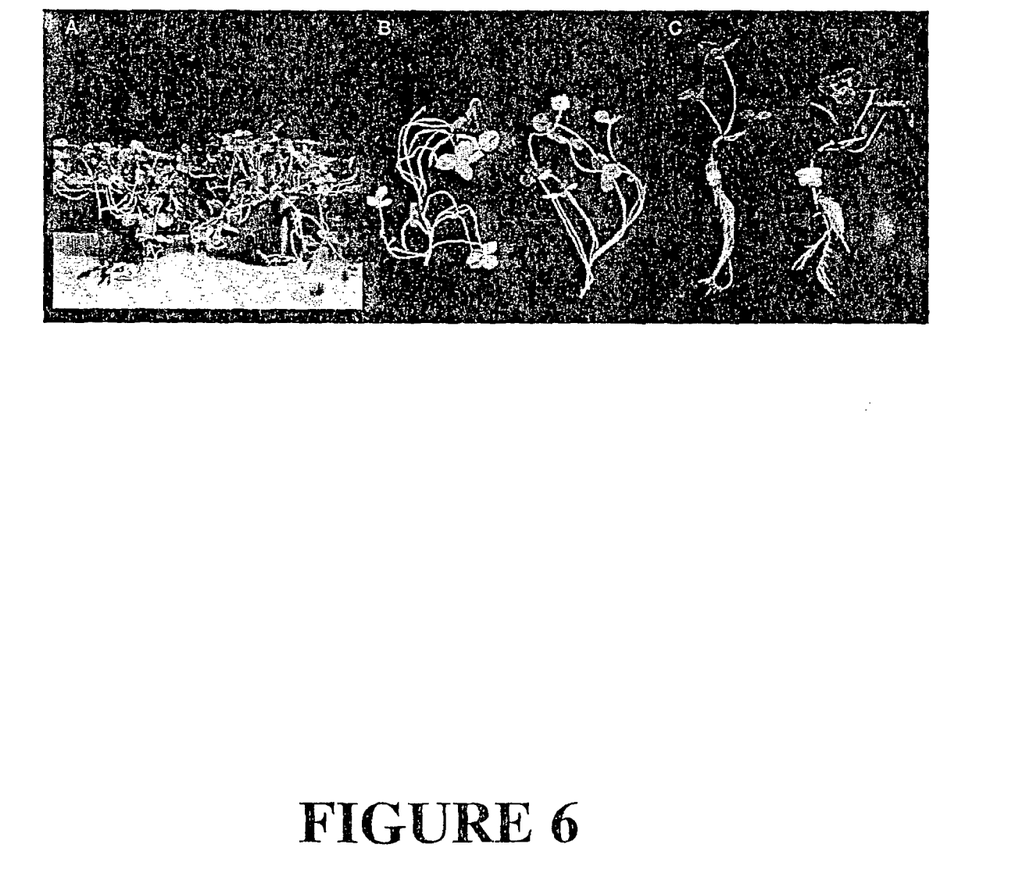
FIG. 6 shows A) General plant morphology, B) Normal shoot development, and C) Normal root development in atmyb32:::ipt transgenic white clover (*T. repens*) (right) plants compared to control plants (left).

Normal plant morphology as well as normal shoot and normal root development was observed in atmyb32:ipt transgenic white clover plants (FIG. 6), thus indicating that the regulated expression of the ipt gene under control of the atmyb32 promoter did not negatively affect neither rooting nor apical dominance of the transgenic white clover plants (Table 1).

TABLE 1

| Transformant | Cultivar | Construct | ipt copy No | Phenotype |
|---|---|---|---|---|
| Hmi01 | Haifa | atmyb32::ipt | 1 | Normal |
| Hmi08 | Haifa | atmyb32::ipt | >3 | Normal |
| Imi06 | Irrigation | atmyb32::ipt | 1 | Normal |
| Imi07 | Irrigation | atmyb32::ipt | 3 | Normal |
| Imi09 | Irrigation | atmyb32::ipt | >3 | Normal |
| Imi10 | Irrigation | atmyb32::ipt | >3 | Normal |
| Imi11 | Irrigation | atmyb32::ipt | 1 | Normal |
| Imi12 | Irrigation | atmyb32::ipt | 2 | Normal |
| Imi16 | Irrigation | atmyb32::ipt | 2 | Normal |
| Imi18 | Irrigation | atmyb32::ipt | 1 | Normal |

Normal plant morphology and normal rooting was observed in ten independent atmyb32::ipt transgenic white clover lines analyzed. Estimated ipt gene copy numbers in the ten independent atmyb32::ipt transgenic white clover lines are shown.

It will be understood that the invention disclosed and defined in this specification extends to all alternative combinations of two or more of the individual features mentioned or evident from the text or drawings. All of these different combinations constitute various alternative aspects of the invention.

Finally, it is to be understood that various alterations, modifications and/or additions may be made without departing from the spirit of the present invention as outlined herein.

It will also be understood that the term "comprises" (or its grammatical variants) as used in this specification is equivalent to the term "includes" and should not be taken as excluding the presence of other elements or features.

Documents cited in this specification are for reference purposes only and their inclusion is not an acknowledgement that they form part of the common general knowledge in the relevant art.

The invention claimed is:

1. A method of manipulating senescence in a plant, plant cell, plant seed or other plant part, said method comprising introducing into said plant, plant cell, plant seed or other plant part a genetic construct comprising the myb gene promoter of SEQ ID NO:1, operably linked to the isopentenyl transferase (ipt) gene of SEQ ID NO:2.

2. The method according to claim 1, wherein said genetic construct is introduced into said plant, plant cell, plant seed or other plant part by transduction, transfection or transformation of plant cells.

3. The method according to claim 2, wherein said plant cell comprising the genetic construct is selected and then cultured to regenerate a transformed plant.

4. A vector comprising the myb gene promoter of SEQ ID NO:1 operably linked to the isopentyl transferase (ipt) gene of SEQ ID NO:2.

5. A transgenic plant cell, plant, plant seed or other plant part with modified senescence characteristics, said plant cell, plant, plant seed or other plant part comprising the vector according to claim 4.

6. A transgenic plant cell, plant, plant seed or other plant part with modified senescence characteristics, said plant cell, plant, plant seed or other plant part produced by the method according to claim 1.

* * * * *